United States Patent [19]

Marquis et al.

[11] Patent Number: 4,992,566

[45] Date of Patent: Feb. 12, 1991

[54] RECOVERY OF TERTIARY BUTYL HYDROPEROXIDE AND TERTIARY BUTYL ALCOHOL

[75] Inventors: Edward T. Marquis, Austin; Kenneth P. Keating, Georgetown; John R. Sanderson, Leander; Robert A. Meyer, Austin, all of Tex.

[73] Assignee: Texaco Chemical Company, White Plains, N.Y.

[21] Appl. No.: 401,381

[22] Filed: Aug. 31, 1989

[51] Int. Cl.$^5$ ............................................ C07D 301/19
[52] U.S. Cl. ..................................................... 549/529
[58] Field of Search ........................................ 549/529

[56] References Cited

U.S. PATENT DOCUMENTS 3,819,663  6/1974  Levine et al. ........................ 549/529

Primary Examiner—Glennon H. Hollrah
Assistant Examiner—Ba K. Trinh
Attorney, Agent, or Firm—Jack H. Park; Kenneth R. Priem; Carl G. Ries

[57] ABSTRACT

Tertiary butyl hydroperoxide and tertiary butyl alcohol are recovered from the reaction product formed by reacting excess propylene with tertiary butyl hydroperoxide in solution in tertiary butyl alcohol in the presence of a soluble molybdenum catalyst, by fractionating the reaction produce to provide distillate propylene, propylene oxide, and tertiary butyl alcohol fractions and a heavy distillation fraction comprising tertiary butyl hydroperoxide, tertiary butyl alcohol and impurities, including dissolved molybdenum catalyst, the tertiary butyl hydroperoxide and tertiary butyl alcohol being recovered from the heavy distillation fraction by vacuum evaporation under evaporation conditions including a temperature of about 25° to about 160° C. and a pressure of about 2 to about 200 mm Hg. in order to provide a lighter condensate fraction comprising about 60 to about 95 wt. % of the heavy distillation fraction and containing from about 70 to about 95 wt. % of tertiary butyl alcohol, about 1 to about 20 wt. % of the tertiary butyl hydroperoxide and from about 15 to about 3 wt. % of impurities and also into a clear liquid heavier residue fraction comprising tertiary butyl alcohol, tertiary butyl hydroperoxide and substantially all of the soluble molybdenum catalyst originally contained in the heavy liquid fraction.

10 Claims, 1 Drawing Sheet

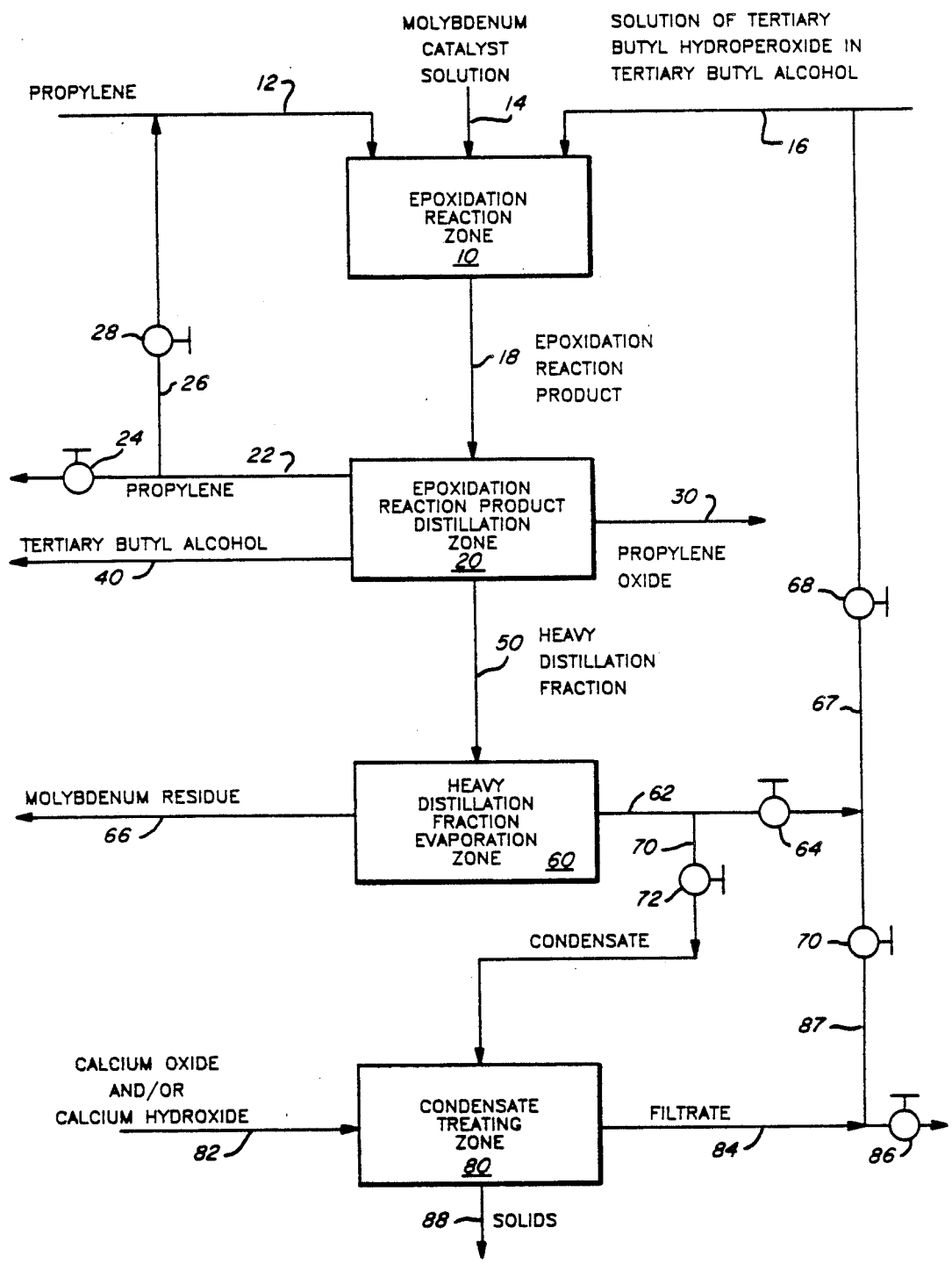

RECOVERY OF TERTIARY BUTYL HYDROPEROXIDE AND TERTIARY BUTYL ALCOHOL

BACKGROUND OF THE INVENTION

1. Field of the Invention

This invention relates to the recovery of tertiary butyl hydroperoxide and tertiary butyl alcohol from a heavy distillation fraction comprising tertiary butyl hydroperoxide, tertiary butyl alcohol and impurities, including dissolved molybdenum catalyst.

More particularly, this invention relates to the recovery of tertiary butyl hydroperoxide and tertiary butyl alcohol from a heavy distillation fraction comprising tertiary butyl hydroperoxide, tertiary butyl alcohol and impurities, including dissolved molybdenum catalyst which remains after a distillate propylene fraction, a distillate propylene oxide fraction and a distillate tertiary butyl alcohol fraction are removed, by distillation, from the reaction product formed by the reaction of excess propylene with tertiary butyl hydroperoxide in solution in tertiary butyl alcohol in the presence of a soluble molybdenum catalyst.

Still more particularly, this invention relates to the separation of a heavy distillation fraction comprising tertiary butyl hydroperoxide, tertiary butyl alcohol and impurities, including dissolved molybdenum catalyst in appropriate vacuum evaporation equipment such as a thin film evaporator, a wiped film evaporator, a forced circulation evaporator, etc., under evaporation conditions including a temperature of about 25° to about 160° C. and a pressure of about 2 to about 200 mm Hg. into a lighter condensate fraction comprising about 60 to about 95 wt. % of the heavy distillation fraction and containing from about 70 to about 95 wt. % of tertiary butyl alcohol, about 1 to about 20 wt. % of the tertiary butyl hydroperoxide and from about 15 to about 3 wt. % of impurities and also into a clear liquid heavier residue fraction comprising tertiary butyl alcohol, tertiary butyl hydroperoxide and impurities including substantially all of the soluble molybdenum catalyst originally contained in the heavy liquid fraction.

In the past, the heavy distillation fraction remaining after removing unreacted propylene, propylene oxide and tertiary butyl alcohol from the reaction product formed by the reaction of excess propylene with tertiary butyl hydroperoxide in solution in tertiary butyl alcohol in the presence of a soluble molybdenum catalyst has generally been considered to be a "waste" product to be treated for the recovery of molybdenum therefrom in order to permit use of the molybdenum-free components as fuel.

It is surprising that evaporation conditions have been discovered that are sufficiently mild to permit the evaporation of tertiary butyl hydroperoxide and tertiary butyl alcohol in the presence of comparatively large quantities of molybdenum and organic acids without the concommitment dehydration of the tertiary butyl alcohol to isobutylene and water and the decomposition of the tertiary butyl hydroperoxide to tertiary butyl alcohol and water.

It is also surprising that the same evaporation conditions are severe enough to permit the substantially quantitative concentration of molybdenum in a heavier bottoms or residue fraction that remains liquid and easy to handle.

2. Prior Art

A process for the coproduction of an epoxide such as propylene oxide with an alcohol such as tertiary butyl alcohol is disclosed and described in Kollar U.S. Pat. Nos. 3,350,422 and 3,351,635. When the olefin is propylene and the hydroperoxide is tertiary butyl hydroperoxide, the principal reaction products are propylene oxide and tertiary butyl alcohol.

Numerous patents have issued describing improvements in the process, such as Russell U.S. Pat. No. 3,418,340, Stein et al. U.S. Pat. No. 3,849,451 and Wu et al. U.S. Pat. No. 4,217,287.

Numerous patents have also issued which are directed to the preparation of molybdenum catalysts useful in catalyzing the reaction of propylene with tertiary butyl hydroperoxide to form propylene oxide and tertiary butyl alcohol such as Mattucci et al. U.S. Pat. No. 3,668,227, Lines et al. U.S. Pat. No. 4,009,122, Brewster U.S. Pat. No. 4,192,578 and Marquis et al. U.S. Pat. Nos. 4,650,886, 4,654,427, 4,703,027 and 4,758,681.

In accordance with molybdenum catalyzed epoxidation processes such as those described in the references, propylene and tertiary butyl hydroperoxide are reacted in solution in tertiary butyl alcohol in an epoxidation reaction zone in the presence of a soluble molybdenum catalyst under epoxidation reaction conditions to form an epoxidation reaction product which is discharged from the epoxidation reaction zone and charged to a distillation zone containing an appropriate number of distillation columns wherein the epoxidation reaction product is typically resolved into a distillate propylene recycle fraction, a distillate propylene oxide product fraction and a distillate tertiary butyl alcohol fraction. A heavy liquid distillation fraction, normally a bottoms fraction, will remain after the separation of the unreacted propylene, the propylene oxide and the tertiary butyl alcohol which will be composed of unreacted tertiary butyl hydroperoxide, tertiary butyl alcohol, impurities and the dissolved molybdenum catalyst.

Levine U.S. Pat. No. 3,819,663 is directed to a method for treating a heavy distillation fraction of this nature in order to recover the molybdenum in the concentrated bottoms fraction for recycle to the epoxidation reaction zone as makeup catalyst.

Levine conducts his wiped-film evaporation process under conditions including a temperature of about 550°-650° F. (about 273° to about 330° C.) at atmospheric pressure to obtain his desired residual fraction for recycle as catalyst makeup and a distillate fraction comprising about 85% or more of the heavy distillation fraction.

Moreover, the high temperatures used by Levine and the concentration of molybdenum in his wiped film evaporator are such that at least partial dehydration of the tertiary butyl hydroperoxide and tertiary butyl alcohol will occur. One of Levine's objectives is the provision of a molybdenum-free overhead that can be burned as a fuel. Although Levine states that the distillate fraction can be worked up for recovery of individual components contained therein, he neither teaches nor describes any technique or equipment that could be used for this purpose.

In U.S. Pat. No. 4,445,283, Sweed describes a process for evaporation of the heavy distillation fraction in order to provide a spent catalyst solution containing between about 0.1 and 2.0 wt. % of molybdenum. The evaporation is accomplished under special evaporation conditions at a pressure of less than about 400 mm Hg in a circulation evaporator and heating means designed so that the feed to the evaporator is not preheated under pressure.

Thornton et al. U.S. Pat. No. 4,584,413 discloses a process for removing contaminating quantities of primary and secondary alkyl hydroperoxides from tertiary butyl hydroperoxide formed by the oxidation of isobutane by mixing an isobutane oxidation product such as one comprising tertiary butyl hydroperoxide, tertiary butyl alcohol and oxygenated by-products including primary and secondary alkyl hydroperoxides with an aqueous solution of an alkali metal or alkaline earth metal hydroxide followed by distillation of the mixture to obtain a tertiary butyl alcohol fraction and a two-phase tertiary butyl hydroperoxide azeotrope fraction, the tertiary butyl hydroperoxide phase of which is neutralized in order to provide a more purified tertiary butyl hydroperoxide product.

SUMMARY OF THE INVENTION

In accordance with the present invention, a heavy distillation fraction comprising tertiary butyl hydroperoxide, tertiary butyl alcohol, impurities and dissolved molybdenum catalyst resulting from the removal of propylene, propylene oxide and tertiary butyl alcohol from an epoxidation reaction product is further fractionated in a falling film, wiped-film, or forced circulation evaporator under evaporating conditions including a temperature of about 25° to about 160° C. and a pressure of about 2 to about 200 mm Hg in order to obtain an overhead fraction comprising about 60 to about 95 wt. % of the charged heavy distillation fraction and where said overhead fraction is composed of from about 70 to about 96 wt. % of tertiary butyl alcohol and about 1 to about 20 wt. % of tertiary butyl hydroperoxide.

When propylene is reacted with tertiary butyl hydroperoxide in solution in tertiary butyl alcohol in an epoxidation reaction zone in the presence of a soluble molybdenum catalyst to form propylene oxide and additional tertiary butyl alcohol, an epoxidation reaction mixture is formed which will contain not only unreacted feed components and the desired propylene oxide and tertiary butyl alcohol, but also the soluble molybdenum catalyst and impurities including oxygen-containing impurities and hydrocarbon impurities such as methyl formate, acetone, isobutyraldehyde, methanol, isopropyl alcohol, ditertiary butyl peroxide, formic acid, acetic acid, isobutyric acid, methyl formate, methyl acetate, methyl isobutyrate, etc., and hydrocarbons resulting from the undesired polymerization of propylene such as hydrocarbons containing 6 or more carbon atoms.

Although most of the impurities are present in the epoxidation reaction mixture in minor quantities, they are progressively concentrated as the epoxidation reaction product is resolved by distillation into a propylene recycle fraction, a propylene oxide product fraction and a tertiary butyl alcohol product fraction, all of which are distillate fractions, and a heavier distillation fraction, typically a bottoms fraction, having the composition generally as specified in Table I.

TABLE I

| COMPOSITION OF HEAVY DISTILLATION FRACTION | |
|---|---|
| Component | Wt. % Range |
| Oxygenates lighter than TBA (such as acetaldehyde, acetone, | 0.1–2.0 |

TABLE I-continued

| COMPOSITION OF HEAVY DISTILLATION FRACTION | |
|---|---|
| Component | Wt. % Range |
| IPA, etc.) | |
| Tertiary butyl alcohol (TBA) | 70.0–90.0 |
| Oxygenates heavier than TBA and lighter than TBHP in the GLC | 1.0–4.0 |
| Tertiary butyl hydroperoxide (TBHP) | 2.0–20.0 |
| Heavies (heavier than TBHP in the GLC, largely the propylene glycol t-butyl ethers | 3.0–12.0 |
| Molybdenum concentration | 500–5,000 ppm |

This fraction is hereafter sometimes referred to, especially in the Working Examples, as the "catalyst bottoms".

According to the present invention, this heavy distillation fraction is used as a charge stock for a falling film, wiped-film or forced circulation evaporator which is operated under evaporating conditions such as a temperature of about 25° to about 160° C., such as about 50° to 100° C. and a pressure of 2 to about 200 mm Hg. The heavy liquid distillation fraction is resolved in the falling film, wiped-film or forced circulation evaporator, into an overhead fraction comprising from about 60 to about 95 wt. % of the charged heavy liquid residue fraction and a bottoms fraction comprising the balance.

The heavy liquid distillation bottoms fraction that is obtained by the process of the present invention is a liquid fraction which can be handled with comparative ease insofar as its disposal is concerned. Typically, this heavy residual fraction will be sold to a company that reclaims metals from hydrocarbon fractions in order that the molybdenum contained therein may be recovered for reuse.

The evaporated overhead fraction obtained in the falling film, wiped-film or forced circulation evaporator will typically contain from about 60 to about 95 wt. % of tertiary butyl alcohol, about 1 to about 20 wt. % of tertiary butyl hydroperoxide and, correspondingly, from about 15 to about 3 wt. % of impurities, principally oxygen-containing impurities having boiling points of less than about 250° C. at atmospheric pressure. Among the impurities that will typically be present are impurities such as formic acid, acetic acid and isobutyric acid, propylene glycol esters, etc.

If the lighter evaporated overhead condensate fraction from the vacuum evaporation equipment (e.g., a falling film evaporator, a wiped film evaporator, a forced circulation evaporator, etc.) has an acid number of less than about 12 meq/g, it can usually be recycled directly to the epoxidation reaction zone.

If the lighter evaporated condensate fraction has an acid number of more than about 12 meq/g, it is usually unsuitable for direct recycle because of the high content of carboxylic acids, which will normally lead to poor propylene oxide selectivities because the high acidity promotes reaction of propylene oxide with alcohols present in the reaction mixture.

In this situation, however, the lighter evaporated condensate fraction can be treated with calcium oxide and/or hydroxide in the manner disclosed and claimed in copending Marquis et al. U. S. patent application Ser. No. 07/400,901, filed Aug. 30, 1989 and entitled "Removal of Acidic Contaminants from Tertiary Butyl Hydroperoxide". Thus, the lighter evaporated condensate fraction can be charged to a treating zone and treated with about ½ to 1 equivalents of calcium oxide and/or calcium hydroxide, based on the carboxylic acid content of the condensate fraction to form a slurry of partially precipitated carboxylic acid impurities. The precipitate may be separated from the treated product by any suitable means such as centrifugation, filtration, etc., to provide a filtrate that is suitable for recycle to the epoxidation reaction zone, in that precipitation of the molybdenum catalyst will not result from the recycle operation.

BRIEF DESCRIPTION OF THE DRAWING

In the drawing, the FIGURE is a schematic diagram of the reaction and purification sequence that is used in the course of the present invention for the recovery of tertiary butyl alcohol and tertiary butyl hydroxide from a heavy distillation fraction recovered from the reaction product formed by the reaction of propylene with tertiary butyl hydroxide in the presence of a soluble molybdenum catalyst to provide propylene oxide and additional tertiary butyl alcohol.

DESCRIPTION OF THE PREFERRED EMBODIMENT

Turning now to the drawing, there is shown a schematic flowsheet illustrating a preferred method of practicing the process of the present invention.

An epoxidation reaction zone 10 is provided and propylene is charged thereto by a line 12 together with a soluble molybdenum catalyst charged by a line 14 and a solution of tertiary butyl hydroperoxide and tertiary butyl alcohol charged by a line 16.

The epoxidation reaction is an epoxidation reaction of the type disclosed by Kollar U.S. Pat. No. 3,351,653 as further elaborated upon, for example, in British patent specification No. 1,298,253 wherein propylene is reacted with tertiary butyl hydroperoxide under reaction conditions including a reaction temperature within the range of about 180° to about 300° F., a pressure of about 300 to about 1000 psig. and, more preferably, a temperature of about 220° F. to about 280° F. and a pressure of about 500 to about 800 psig.

The soluble molybdenum catalyst charged to the epoxidation reaction zone by the line 14 may be an epoxidation catalyst of the type known in the art such as those disclosed by the Kollar patent or the British patent or by Marquis et al. U.S. Pat. Nos. 4,626,596, 4,650,886, 4,654,427, or 4,758,681. The Marquis et al. patents are directed to molybdenum/alkanol complexes such as solutions of molybdenum compounds in ethylene glycol which contain a high concentration of molybdenum and are particularly useful as catalysts in the epoxidation reaction. Marquis et al. teach, for example, the epoxidation of propylene with tertiary butyl hydroperoxide with their catalyst under epoxidation conditions including a temperature of 50° to 180° C. and a use of propylene to tertiary butyl hydroperoxide ratios within the range of about 0.9:1 to about 3.0:1.

Suitably, the tertiary butyl hydroperoxide that is charged to the epoxidation reaction zone 10 by way of line 16 is about a 40 to about 75 wt. % solution of tertiary butyl hydroperoxide in tertiary butyl alcohol. The catalyst is charged to the epoxidation reaction zone 10 by the charge line 14 in an amount such as to provide from about 50 to about 1000 ppm of molybdenum, based on the total of the reactants charged and, more preferably, from about 200 to 600 ppm. The reaction is preferably conducted at superatmospheric pressure such as a pressure of about 300 to 1000 psig.

When the reaction is conducted on a continuous basis, as illustrated in the drawing, the feed materials are charged to the epoxidation reaction zone 10 through the lines 12, 14 and 16 at rates sufficient to maintain the desired concentration of reactants and an equivalent volume of epoxidation reaction mixture is withdrawn from the epoxidation reaction zone 10 by way of a discharge line 18. The reaction product discharged by the line 18 will normally comprise unreacted propylene, a minor amount of unreacted tertiary butyl hydroperoxide, propylene oxide, tertiary butyl alcohol, including tertiary butyl alcohol formed by the reaction of the tertiary butyl hydroperoxide with propylene, the molybdenum catalyst and impurities such as propane, propionaldehyde, acetone, methanol, isopropanol, water, acetaldehyde, methyl formate, acetic acid, formic acid, isobutyric acid, hydrocarbons containing 6 or more carbon atoms and high boiling residue components.

The reaction product 18 is charged to an epoxidation reaction product distillation zone 20 where it is separated by distillation into desired fractions in accordance with methods known to those skilled in the art. For example, the distillation sequence disclosed in British Pat. No. 1,298,253 may be used.

One of the distillate products that is recovered in the zone 20 is a propylene fraction which is discharged by a line 22 controlled by a valve 24 and provided with a branch line 26 controlled by a valve 28 in order to permit the recycle of unreacted propylene to the epoxidation reaction zone 10 through the propylene charge line 12.

Another distillate fraction that is obtained is a propylene oxide product fraction 30 which is discharged by the line 30. The propylene oxide product fraction may be purified in the epoxidation reaction distillation zone 20 by known techniques such as, for example, those disclosed in Burnes et al. U.S. Pat. No. 3,715,284, Schmidt et al. U.S. Pat. No. 3,909,366, Schmidt U.S. Pat. No. 3,881,996, Jubin U.S. Pat. No. 3,607,669, Schmidt U.S. Pat. No. 3,843,488 or Schmidt U.S. Pat. No. 4,140,588.

Another product that is recovered from the epoxidation reaction product distillation zone 20 is a tertiary butyl alcohol distillate product 40 which may be further purified, if desired, to remove oxygenated impurities therefrom by catalytic treatment as disclosed, for example, in Sanderson et al. U.S. Pat. No. 4,704,482, Sanderson et al. U.S. Pat. No. 4,705,903 or Sanderson et al. U.S. Pat. No. 4,742,149.

A heavy distillation fraction 50, usually a bottoms fraction, is also discharged from the epoxidation reaction zone 20. As described by Levine U.S. Pat. Nos. 3,819,663 and Sweed 4,455,283, the heavy distillation fraction will contain substantially all of the molybdenum catalyst initially charged to the epoxidation reaction zone 10 by way of the line 14. The heavy distillation fraction 50 will contain other products such as tertiary butyl hydroperoxide, tertiary butyl alcohol and impurities including oxygenates lighter than tertiary butyl alcohol such as acetaldehyde, acetone, isopropyl alcohol, etc., oxygenates heavier than tertiary butyl alcohol but lighter than tertiary butyl hydroperoxide, and residue components heavier than tertiary butyl hydroperoxide such as propylene glycol tertiary butyl ethers, hydrocarbons containing 6 or more carbon atoms, etc. As indicated, the heavy distillation fraction 50 will also contain carboxylic acids such as formic acid, acetic acid and isobutyric acid.

In accordance with the present invention, the heavy distillation fraction 50 is charged to a heavy distillation evaporation zone 60 which may comprise, for example, a wiped-film evaporator, a falling film evaporator, a forced circulation evaporator, etc., which is operated at a subatmospheric pressure within the range of about 2 to about 200 mm Hg. and at a temperature of about 50° to about 160° C. with a residence time such that from about 60 to about 95 wt. % of the heavy distillation fraction charged by the line 50 is taken overhead as condensate by a discharge line 62 controlled by a valve 64. The remaining 40-5 wt. % of the material charged to the evaporation zone 60 by the line 50 will be discharged by way of a line 66 and will contain substantially all of the molybdenum initially charged to the epoxidation reaction zone 10.

It has been surprisingly discovered in accordance with the present invention that when the fraction 50 is subjected to evaporation in the manner described and under the conditions described, decomposition of tertiary butyl hydroperoxide to tertiary butyl alcohol and/or decomposition of tertiary butyl alcohol to isobutylene is substantially inhibited so that decomposition of the material charged to the evaporator 60 by the line 50 is minimal.

If the overhead fraction 62 discharged from the evaporator 60 by way of the line 62 has an acid number of about 12 or less, it may be charged directly to a tertiary butyl hydroperoxide recycle line 66 controlled by a valve 68. If the acid number is higher, the fraction 62 may be routed by a branch line 70 controlled by a valve 72 in order to reduce the acid number to an acceptable level. This is preferably done by treatment of the fraction 70 with calcium oxide and/or calcium hydroxide in accordance with the Marquis et al. copending patent application mentioned above wherein it is shown that the treatment of the fraction 70 with ½ to 1 equivalents of calcium oxide and/or calcium hydroxide, based on the carboxylic acid content of the fraction 70, will partially precipitate the carboxylic acids contained in the fraction 70 and will reduce the acidity of the stream 70. If this is done, the calcium oxide and/or calcium hydroxide is charged to a condensate treating zone 80 by a charge line 82 and the treated condensate in the line 70 is separated into a solids filtrate fraction by centrifugation, filtration, etc., to form a solids fraction stream 88 containing carboxylic acid salts. The reduced-acidity filtrate is discharged from the condensate treating zone 80 by a line 84 controlled by a valve 86 which is provided with a branch line 87 controlled by a valve 90 leading to the tertiary butyl hydroperoxide recycle line 66.

In accordance with the present invention, the heavy liquid distillation fraction 50 discharged from the column 20 is charged by way of line 50 to a wiped film, rotary or forced circulation evaporator 60 wherein the operating conditions include a temperature within the range of about 50° to about 160° C. and a pressure within the range of about 2 to about 200 mm Hg, the average residence time of the fraction 50 in the evaporator 60 being such that from about 60 to about 95 wt. % of the material charged by way of the line 50 is taken overhead as a condensate fraction by way of the line 62; the remaining 40-5 wt. % of the material charged by way of the line 50 being discharged from the evaporator 60 by way of a bottoms discharge line 66. The fraction 66 will contain substantially all of the molybdenum initially discharged from the epoxidation reaction zone 10.

It has been surprisingly discovered in accordance with the present invention that when the fraction 50 is subjected to evaporation in the manner described and under the conditions described, decomposition of tertiary butyl hydroperoxide to tertiary butyl alcohol and/or the decomposition of tertiary butyl alcohol to isobutylene is substantially inhibited so that decomposition of the material charged to the evaporator 60 by the line 50 is minimal.

If the fraction 62 discharged from the evaporator 60 by way of the line 62 has an acid number of about 12 or less, it may be charged directly to the tertiary butyl hydroperoxide charge line 14. If the acid number is higher, the distillate fraction 62 may be treated with CaO or Ca(OH)$_2$ (reference to application concerning acidity reduction TBHP/TBA and affording an epoxidizing feed stream low in acidity yet will not precipitate moly) in order to reduce the acid number to an acceptable level after which the thus treated stream will be recycled to the epoxidation reaction zone by way of the charge line 16.

For example, the distillate fraction 62 may be treated with CaO or Ca(OH)$_2$ which will react with any acid such as acetic acid, formic acid or isobutyric acid present in the fraction 62 in order to form salts such a the calcium salts which can be removed by filtration and after water wash of this TBHP/TBA stream it can be recycled to the epoxidation reactor.

EXAMPLES

The following specific examples are given by way of illustration of the manner in which the process of the present invention may be practiced on a batch basis. Where parts are mentioned they are parts by weight unless otherwise indicated. The examples are given by way of illustration and not as limitations on the scope of this invention.

As used in the examples, the term "epoxidation catalyst bottoms" refers to a stream obtained from an epoxidation reactor effluent after unreacted propylene, low boiling byproducts, propylene oxide, byproducts such as methanol and acetone and most of the tertiary butyl alcohol have been removed by distillation as distillate products.

EXAMPLE 1A (6195-25)

Epoxidation catalyst bottoms were the feed used in this wiped-film evaporator run in which conditions were found that result in the quantitative recovery of the unreacted TBHP present in epoxidation catalyst bottoms. The epoxidation of propylene was accomplished by reacting t-butyl hydroperoxide (TBA solution) with propylene in the presence of a molybdenum catalyst. Unreacted propylene, low boiling byproducts, propylene oxide and a portion of t-butyl alcohol were recovered in conventional distillation columns affording a stream called "epoxidation catalyst bottoms", containing 9.48 wt. % TBHP (by wet titration), and 677 ppm molybdenum. Using a A. H. Thomas Rota-Still wiped-film evaporator, 500.0 grams of epoxidation catalyst bottoms were fed to the wiped film evaporator (WFE) with the wall temperature maintained at 80°-85° C. and the pressure adjusted to 20 mm Hg. Overhead amounting to 432.4 grams was recovered with bottoms amounting to 64.2 grams recovered. Total material recovered amounted to 496.6 grams or an overall material recovery of 99.3%. The overhead was titrated and found to contain 37.86 grams of TBHP, while the bottoms contained 9.52 grams of TBHP for an overall TBHP recovery or balance of 47.38 grams compared to TBHP feed of 500.0 grams×9.48% or 47.40 grams, the overall TBHP recovery or balance was essentially quantitative (99.96%). The TBHP recovered overhead represents 80% of that recovered with 20% of the TBHP remaining in the bottoms. The quantitative recovery of TBHP without decomposition to TBA (and further to isobutylene and water) is remarkable in light of the 5600 ppm molybdenum catalyst level in the bottoms recovered from the wiped-film evaporator. Clearly, the use of low evaporation temperatures and reduced pressures adjusted so that not too much overhead is taken (and thereby causing scorching or deposition of solids on the evaporation walls) results in the smooth, solids-free operation described. The overheads were water white and the bottoms were a light yellow mobile (at ambient temperatures) liquid with no solids. Atomic absorption analysis on the bottoms further indicated a quantitative recovery of molybdenum. Water analysis of overheads and bottoms further indicates a near zero make of water during the evaporation. The epoxidation catalyst bottoms feed to the WFE (500 g) contained 404.615 g TBA (80.923 wt. %). The overhead (432.4 g) contained 361.311 g TBA while the WFE bottoms (64.2 g) contained 41.094 g TBA. Total TBA recovered was 402.615 g versus 404.615 g fed. TBA recovery was 99.6%.

EXAMPLE 1B (6195-3)

In a batch process, 500.0 grams of catalyst bottoms (wt. % TBHP=12.52%, ppm molybdenum=729 ppm, acid number=15.80 mg KOH/g sample) were evaporated using a rotary evaporator with the bath temperature set at 70° C. The catalyst bottoms were evaporated for one hour and 55 minutes (1.92 hours) using a vacuum that ranged from 20-30 mm Hg. The overall material balance was 98.7%. Overhead and bottoms recovered were 493.5 g of the 500 grams charged. Of the 493.5 g recovered 13.4% of the material was in the bottoms and 86.6% was in the overhead. Of the 62.60 grams of TBHP fed to the evaporation 62.02 grams of TBHP were recovered in the overhead and bottoms (99.1% TBHP recovery). Of the 62.02 g of TBHP recovered, 78.5% of TBHP was taken overhead and 21.5% remained in the bottoms. The overhead material, comprised of about 80% TBA and 14% TBHP would be suitable for recycle to the epoxidation reaction provided sufficient acidity would be removed from this stream to allow addition of the recycle TBHP to the peroxidate without increasing the acidity of this stream to the epoxidizer. The bottoms from these concentration experiments contained approximately 8000 ppm moly (0.83 wt. % moly) and were a mobile yellow liquid flowing freely at room temperature.

EXAMPLE 2A (6195-26)

In an experiment exactly like 1A above, 500 grams of catalyst bottoms (9.487% TBHP, 677 ppm moly, and acid number 14.10 mg KOH/g) were evaporated using a rotary evaporator with the bath temperature maintained at 73°-90° C. for 5 minutes (15 mm), followed by 3 minutes at 90°-100° C. (15 mm) and finally 2 minutes at 100°-110° C. (15 mm). The TBHP recovered in the overheads and bottoms amounted to 100.2% of that charged to the evaporator. Of the 47.48 g of TBHP recovered, 46.65 g (98.3%) of TBHP were recovered overhead with only 0.83 grams remaining in the bottoms (1.7%). The bottoms from this concentration contained 2.36 % molybdenum and were a mobile liquid, light yellow in color.

EXAMPLE 3A (6195-40)

In a continuous evaporation experiment some 3450.2 g of epoxidation catalyst bottoms were fed to the rotary evaporator at pressures of 15-30 mm and bath temperatures of 5082° C. and the evaporation took a total of 3.50 hours. Overall material balance overheads and bottoms amounted to 3418.7 g (99.1% recovery). TBHP recovered in the overhead and bottoms amounted to 325.99 g out of 327.08 g fed (99.7% recovery). TBHP remaining in the bottoms amounted to 2.7% of that recovered while that coming overhead amounted to 97.3% of that recovered. The bottoms were a mobile, light yellow liquid (1.50% moly). TBA recovered in the overhead amounted to 2672.4 g whereas 15.2 g of TBA were recovered in the bottoms. Overall TBA recovery was 2687.6 g (96.3% of that fed).

Table II is included to show that TBHP when first heated in the presence of molybdenum at 120°-125° C. for 1-2 hours without allowing distillation of TBA/TBHP affords substantial decomposition of TBHP.

TABLE II

| Ex. | Conditions Temp, Time | ppm Moly in Feed | Wt. % Formic in Feed | Wt. % PG in Feed | Wt. % TBHP in Feed* | Wt. %* TBHP in treated Material | % TBHP Decomposition |
|---|---|---|---|---|---|---|---|
| 1 | 100° C., 1 hr. | 1000 | 0.0 | 9.2 | 9.806 | 8.906 | 9.18 |
| 2 | 125° C., 1 hr. | 1000 | 0.0 | 0.0 | 9.656 | 8.199 | 15.09 |
| 3 | 125° C., 1 hr. | 1000 | 0.0 | 9.2 | 9.537 | 2.843 | 70.19 |
| 4 | 125° C., 1 hr. | 5000 | 0.0 | 5.9 | 10.084 | 0.022 | 99.998 |
| 5 | 120° C., 2 hr. | 90.7 | 0.0 | 0.0 | 20.000 | 8.004 | 59.98 |
| 6 | 120° C., 2 hr. | 133.0 | 0.0 | 0.0 | 20.000 | 5.370 | 73.15 |
| 7 | 120° C., 2 hr. | 422.0 | 0.0 | 0.0 | 20.000 | 5.010 | 74.95 |

*by titration

Our invention involves low temperature evaporation in a wiped film, rotary or forced circulation evaporator to avoid TBA dehydration to isobutylene and avoids TBHP decomposition to TBA even in the presence of concentrated moly catalyst. The success is evidenced by our essentially quantitative recovery of TBHP (quantitative material balance of TBHP in overheads and bottoms compared to the TBHP present in the feed). Further, we observe an essentially quantitative recovery of TBA during our low temperature evaporation in the WFE. TBA balances (recovery) were generally >90%.

See Table III for summaries of several other evaporations in which TBHP and TBA are essentially recovered quantitatively.

TABLE III

| Notebook Run # (Example) | Evaporator Type | Conditions Temp. °C. | Time, Hrs. | Vacuum, mm Hg. | Balances Overall Material[1] | Total TBHP Bal.[2] | % Moly. in Btms |
|---|---|---|---|---|---|---|---|
| 6195-3 (Ex 1B) | Rotary | 70 | 1.92 | 20-30 | 98.7 | 99.1 | 0.83 |
| 6195-25 (Ex 1A) | Wiped Film | 80-85 | Very Short | 20 | 99.3 | 100.0 | 0.56 |
| 6195-26 (Ex 2A) | Rotary | 73-110 | 0.17 | 15 | 96.0 | 100.2 | 2.36 |
| 6195-39 | Rotary | 60-84 | 2.99 | 25-40 | 98.5 | 101.0 | 0.87 |
| 6195-40 (Ex 3A) | Rotary | 50-82 | 3.50 | 15-30 | 99.1 | 99.7 | 1.50 |
| 6290-2 | Rotary | 25-80 | 5.08 | 8-30 | 99.9 | 99.6 | 1.37 |
| 6290-3 | Rotary | 25-80 | 5.91 | 6-22 | 99.3 | 98.6 | 1.50 |
| 6290-5 | Rotary | 24-71 | 5.58 | 3-10 | 100.0 | 99.9 | 1.66 |
| 6290-6 | Rotary | 23-90 | 5.25 | 3-28 | 99.7 | 98.3 | 2.93 |
| 6290-20 | Rotary | 26-85 | 5.74 | 1-30 | 99.6 | 99.3 | 1.35 |

[1] Total grams out/total grams fed × 100
[2] Total grams TBHP out/total grams TBHP fed × 100

As is also illustrated by the examples, an advantage of the present invention is the essentially quantitative recovery of unreacted tertiary butyl hydroperoxide from the reactor effluent from the epoxidation reaction product and the recovery of residual quantities of tertiary butyl alcohol with minimal dehydration of the tertiary butyl alcohol to isobutylene.

It is surprising that at the low temperatures described in our evaporation process the tertiary butyl hydroperoxide is not decomposed to tertiary butyl alcohol nor does the tertiary butyl alcohol decompose to form isobutylene. This is surprising because the feed material contains substantial quantities of formic, acetic and isobutyric acid and normally from about 5000 to about 20,000 ppm of molybdenum.

EXAMPLE IV

In a continuous process, epoxidation catalyst bottoms was concentrated with the use of a forced circulation evaporator. The catalyst bottoms were evaporated at a temperature and pressure of 77° C. and 120 mm Hg, respectively. The overall recovery across the unit was 100.1% while component recoveries of TBA and TBHP were 99.1 and 96.4%, respectively. In this particular run, 232 lb. of material was processed, 207.5 lb. was taken overhead and 24.8 lb. remained as bottoms (see Table IV).

TABLE IV

CLASS A MATERIAL - FIRST PASS EVAPORATION
REFERENCE: 6270 FEED 21-01, OVHD 21-33, BTMS 21-34

| Component Balances Species | Weight % Feed | Overhead | Bottoms | Recovery % |
|---|---|---|---|---|
| Lights | 0.133 | 0.365 | 0.057 | 250.0 |
| TBA | 85.761 | 89.589 | 45.288 | 99.1 |
| TBA < X < TBHP | 2.354 | 2.314 | 2.855 | 100.9 |
| TBHP | 2.05 | 1.63 | 4.86 | 96.4 |
| Heavies | 6.966 | 3.300 | 46.169 | 113.1 |
| Moly | 0.0864 | 0.0009 | 0.77 | 96.1 |
| Water | 2.65 | 2.80 | <0.001 | 94.5 |
|  | 100.000 | 99.999 | 100.000 |  |
| GC Factor | 0.97022 | 0.97037 | 0.98756 |  |
| Trace Components/Other Wet Tests |  |  |  |  |
| Iron (ppm) | <0.5 | #### | 5.8 | #### |
| Chromium (ppm) | <0.5 | #### | 0.7 | #### |
| Nickel (ppm) | <0.5 | #### | 6.5 | #### |

TABLE IV-continued

CLASS A MATERIAL - FIRST PASS EVAPORATION
REFERENCE: 6270 FEED 21-01, OVHD 21-33, BTMS 21-34

| | | | | |
|---|---|---|---|---|
| Sodium (ppm) | #### | #### | 3.7 | #### |
| Potassium (ppm) | #### | #### | 1.4 | #### |
| Acid # (mg/g) | 15.27 | 10.28 | 55.97 | 99.3 |

Overall Balance

| Date | Time | Feed | Ovhd | Btms |
|---|---|---|---|---|
| 07/14 | 1500 | 464.00 | 282.00 | 0.00 |
| 07/15 | 1400 | 232.00 | 489.50 | 24.77 |
|  |  |  |  | Recovery % |
|  |  | 232.00 | 207.50 | 24.77 | 100.1 |

% OVHD = 89.4
Operating Conditions  Pressure: 120 mm Hg

BTMS Temperature: 77° C.
OVHD Temperature: 42° C.

Having thus described our invention, what is claimed is:

1. In a process for the preparation of propylene oxide and tertiary butyl alcohol wherein propylene and tertiary butyl hydroperoxide are reacted in an epoxidation reaction zone in solution in tertiary butyl alcohol in the presence of a soluble molybdenum catalyst to provide an epoxidation reaction product comprising unreacted propylene, unreacted tertiary butyl hydroperoxide, tertiary butyl alcohol, dissolved molybdenum catalyst and impurities and wherein the epoxidation reaction product is resolved into product fractions in a distillation zone including a distillate propylene fraction, a distillate propylene oxide fraction, a distillate tertiary butyl alcohol fraction and a heavy liquid distillation fraction composed primarily of tertiary butyl hydroperoxide, tertiary butyl alcohol and impurities, including dissolved molybdenum catalyst, the improvement for fractionating said heavy liquid fraction without substantial decomposition of the tertiary butyl hydroperoxide contained therein to tertiary butyl alcohol and without substantial decomposition of the tertiary butyl alcohol contained therein to isobutylene which comprises:

separating said heavy liquid fraction by vacuum evaporation under evaporator operating conditions including a temperature of about 25° to about 160° C. and a pressure of about 2 to about 200 mm Hg. into an evaporated overhead condensate fraction comprising about 60 to about 95 wt. % of the charged heavy liquid fraction and a clear liquid residue fraction, said heavy liquid fraction comprising about 70 to 90 wt. % tertiary butyl alcohol, about 2 to about 20 wt. % tertiary butyl hydroperoxide, about 500 to 5,000 ppm of molybdenum and impurities, said evaporated overhead fraction containing from about 70 wt. % to about 95 wt. % of tertiary butyl alcohol, about 1 wt. % to about 20 wt. % of tertiary butyl hydroperoxide and, correspondingly, about 15 wt. % to about 3 wt. % of impurities and said clear liquid residue fraction comprising tertiary butyl hydroperoxide, tertiary butyl alcohol and impurities, including substantially all of the molybdenum containing in said heavy liquid fraction, said overhead fraction containing at least about 80 wt. % of the tertiary butyl hydroperoxide contained in said heavy liquid fraction.

2. A process as in claim 1 wherein said heavy liquid fraction is resolved under evaporation conditions including a temperature of about 50° to about 160° C.

3. A process as in claim 2 wherein the evaporator is a wiped film evaporator.

4. A process as in claim 2 wherein the evaporator is a rotary evaporator.

5. A process as in claim 2 wherein the evaporator is a forced circulation evaporator.

6. In a process for the preparation of propylene oxide and tertiary butyl alcohol wherein propylene and tertiary butyl hydroperoxide are catalytically reacted in an epoxidation reaction zone in solution in tertiary butyl alcohol in the presence of a soluble molybdenum catalyst to provide an epoxidation reaction product comprising unreacted propylene, unreacted tertiary butyl hydroperoxide, tertiary butyl alcohol, dissolved molybdenum catalyst and impurities including acetaldehyde, methanol, methyl formate, acetone, ditertiary butyl peroxide, tertiary butyl formate, isobutanol, tertiary butyl ethers of propylene glycol, and carboxylic acids including formic acid, acetic acid, isobutyric acid, etc., and wherein the epoxidation reaction product is resolved into product fractions in a distillation zone including a distillate propylene recycle fraction, a distillate propylene oxide product fraction, a distillate tertiary butyl alcohol product fraction and a substantially anhydrous heavy liquid distillation fraction composed primarily of tertiary butyl hydroperoxide, tertiary butyl alcohol and said impurities, including dissolved molybdenum catalyst and said carboxylic acids, the improvement for fractionating said heavy liquid fraction without substantial decomposition of the tertiary butyl hydroperoxide contained therein to tertiary butyl alcohol and without substantial decomposition of the tertiary butyl alcohol contained therein to isobutylene which comprises:

charging said heavy liquid distillation fraction to a vacuum evaporation zone and resolving said heavy liquid fraction therein under evaporation conditions including a temperature of about 50° to about 160° C. and a pressure of about 2 to about 200 mm Hg. into an evaporated substantially anhydrous overhead condensate fraction comprising about 60 to about 95 wt. % of the charged heavy liquid fraction and a substantially anhydrous clear liquid residue fraction, said heavy liquid fraction comprising about 70 to 90 wt. % tertiary butyl alcohol, about 2 to about 20 wt. % tertiary butyl hydroperoxide, about 500 to 5,000 ppm of molybdenum and impurities, said evaporated overhead fraction containing from about 70 wt. % to about 95 wt. % of tertiary butyl alcohol, about 1 wt. % to about 20 wt. % of tertiary butyl hydroperoxide and, correspondingly, about 15 wt. % to about 3 wt. % of impurities, said overhead fraction containing at least about 80 wt. % of the tertiary butyl hydroperoxide contained in said heavy liquid fraction.

7. A process as in claim 6 wherein the evaporator is a wiped film evaporator.

8. A process as in claim 6 wherein the evaporator is a rotary evaporator.

9. A process as in claim 6 wherein the evaporator is a forced circulation evaporator.

10. In a process for the preparation of propylene oxide and tertiary butyl alcohol wherein propylene and tertiary butyl hydroperoxide are reacted in an epoxidation reaction zone in solution in tertiary butyl alcohol in the presence of a soluble molybdenum catalyst to provide an epoxidation reaction product comprising unreacted propylene, unreacted tertiary butyl hydroperoxide, tertiary butyl alcohol, dissolved molybdenum catalyst and impurities including acetaldehyde, methanol, methyl formate, acetone, ditertiary butyl peroxide, tertiary butyl formate, isobutanol, tertiary butyl ethers of propylene glycol, and carboxylic acids including formic acid, acetic acid, isobutyric acid, etc., and wherein the epoxidation reaction product is resolved into product fractions in a distillation zone including a distillate propylene fraction, a distillate propylene oxide fraction, a distillate tertiary butyl alcohol fraction and a heavy liquid distillation fraction composed primarily of tertiary butyl hydroperoxide, tertiary butyl alcohol and impurities, including dissolved molybdenum catalyst said carboxylic acids, the improvement for fractionating said heavy liquid fraction without substantial decomposition of the tertiary butyl hydroperoxide contained therein to tertiary butyl alcohol and without substantial decomposition of the tertiary butyl alcohol contained therein to isobutylene which comprises:

subjecting said heavy liquid fraction to vacuum evaporation unit evaporator operating conditions including a temperature of about 25° to about 160° C. and a pressure of about 2 to about 200 mm Hg. into an evaporated overhead condensate fraction having an acid number of less than about 12 meq/g and comprising about 60 to about 95 wt. % of the charged heavy liquid fraction and a clear liquid residue fraction, and recycling said lighter condensate fraction to said epoxidation reaction zone, said heavy liquid fraction comprising about 70 to 90 wt. % tertiary butyl alcohol, about 2 to about 20 wt. % tertiary butyl hydroperoxide, about 500 to 5,000 ppm of molybdenum and impurities, said evaporated overhead fraction containing from about 70 wt. % to about 95 wt. % of tertiary butyl alcohol, about 1 wt. % to about 20 wt. % of tertiary butyl hydroperoxide and, correspondingly, about 15 wt. % to about 3 wt. % of impurities and said clear liquid residue fraction comprising tertiary butyl hydroperoxide, tertiary butyl alcohol and impurities, including substantially all of the molybdenum contained in said heavy liquid fraction, said overhead fraction containing at least about 80 wt. % of the tertiary butyl hydroperoxide contained in said heavy liquid fraction.

* * * * *